(12) United States Patent
Vale et al.

(10) Patent No.: US 6,692,744 B2
(45) Date of Patent: Feb. 17, 2004

(54) BETAGLYCAN AS AN INHIBIN RECEPTOR AND USES THEREOF

(75) Inventors: Wylie Vale, La Jolla, CA (US); Kathy A. Lewis, San Diego, CA (US); Peter C. Gray, Encinitas, CA (US); Louise M. Bilezikjian, San Diego, CA (US); Amy L. Blount, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 415 days.

(21) Appl. No.: 09/738,171

(22) Filed: Dec. 15, 2000

(65) Prior Publication Data

US 2001/0049360 A1 Dec. 6, 2001

Related U.S. Application Data

(60) Provisional application No. 60/170,971, filed on Dec. 15, 1999, now abandoned.

(51) Int. Cl.$^7$ ............... A61K 39/395; C07K 16/00; C07K 14/00
(52) U.S. Cl. ............... 424/158.1; 530/387.9; 530/388.1; 530/389.1; 530/350
(58) Field of Search ............ 530/350, 388.1, 530/387.1, 387.9; 429/158.1

(56) References Cited

U.S. PATENT DOCUMENTS

| | | | | |
|---|---|---|---|---|
| 4,864,019 A | * | 9/1989 | Vale et al. | 424/139.1 |
| 5,102,868 A | * | 4/1992 | Woodruff et al. | 514/8 |
| 5,428,011 A | | 6/1995 | Sheth et al. | 514/12 |
| 5,786,179 A | | 7/1998 | Kousoulas et al. | 435/69.7 |
| 5,830,671 A | | 11/1998 | Dennis et al. | 435/7.8 |
| 6,060,460 A | | 5/2000 | Ferguson | 514/54 |

OTHER PUBLICATIONS

Brown et al., Science, Mar. 1999, vol. 283, pp. 2080–2082.*
Alberts et al., Molecular Biology of the Cell, 2nd edition, 1989, p. 552.*
Lewis, K., et al. *Betagylcan Binds Inhibin and can Mediate Functional Antagonism of Activin Signalling.* Nature vol. 404, 2000, pp.411–414.
Chong, H., et al. *Immunocytochemical Localization of Latent Transforming Growth Factor–β1 Activation by Stimulated Macrophages.* Journal of Cellular Physiology vol. 178, 1999, pp. 275–283.
DePaolo, L. *Inhibins, Activins, and Follistatins: The Saga Continues.* P.S.E.B.M. vol. 214, 1997, pp. 328–339.
Chong, H., et al. *Structure and Expression of a Membrane Component of the Inhibin Receptor System.* Endocrinology vol. 141, 2000, pp. 2600–2607.
Kaname, S., et al. *Betaglycan has Multiple Binding Sites for Transforming Growth Factor–β1.* Biochemical Journal vol. 315, 1996, pp. 815–820.
Drapert, L., et al. *Identification of an Inhibin Receptor in Gonadal Tumors From Inhibit α–Subunit Knockout Mice.* The Journal of Biological Chemistry vol. 273, 1998, pp. 398–403.

* cited by examiner

Primary Examiner—Yvonne Eyler
Assistant Examiner—Janet L. Andres
(74) Attorney, Agent, or Firm—Benjamin Aaron Adler

(57) ABSTRACT

Inhibins and activins are protein hormones that reciprocally modulate a diversity of regulatory pathways. Competitive binding experiments revealed that betaglycan, the type III TGF-β receptor, also functions as an inhibin receptor. Betaglycan augments the binding of inhibin to the ActRII activin receptor. By augmenting inhibin binding to ActRII, betaglycan effectively sequesters ActRII away from activin and thereby reduces activin signaling. In addition, the ActRII-betaglycan complex may generate novel signals distinct from those initiated by activin signaling via ActRII and ALK4. Betaglycan is produced in discrete nuclei of the rat brain and by specific cell types within the adult rat pituitary, testis, and ovary. The presence of betaglycan within inhibin-responsive tissues and cell types, together with the ability of this protoglycan to bind inhibin and to confer inhibin sensitivity, is consistent with a role of betaglycan as an inhibin-specific receptor mediating inhibin responses within various tissues.

4 Claims, 8 Drawing Sheets

BETAGLYCAN AS AN INHIBIN RECEPTOR AND USES THEREOF

CROSS REFERENCE TO RELATED APPLICATIONS

This application claims benefit of priority of provisional U.S. Ser. No. 60/170,971, filed Dec. 15, 1999, now abandoned.

FEDERAL FUNDING LEGEND

This invention was produced in part using funds from the Federal government under grant no. HD-13527. Accordingly, the Federal government has certain rights in this invention.

BACKGROUND OF THE INVENTION

1. Field of the Invention

The present invention relates generally to the fields of endocrinology, reproductive biology and cell biology, especially in regard to hormone/growth factor signaling. More specifically, the present invention relates to the identification of an inhibin receptor and uses thereof.

2. Description of the Related Art

Inhibins and activins were initially recognized as protein hormones of gonadal origin that reciprocally modulate follicle stimulating hormone (FSH) production by the anterior pituitary (1). These proteins are disulfide-linked dimers of related polypeptides. Activins consist of two β chains, while inhibins possess a β chain linked to a related but divergent α chain (2). Activins are now known to exert important endocrine, paracrine and autocrine actions in both reproductive and non-reproductive tissues. These actions regulate processes including hormone secretion as well as cell proliferation and differentiation, both during development and in adult animals (1,3). Inhibin generally opposes the actions of activin (4) although there are systems where inhibin is unable to block activin responses (5,6).

Inhibins and activins belong to the transforming growth factor-β (TGF-β) superfamily of growth and differentiation factors (7). Like other characterized members of this family, activins have been shown to signal through two classes of transmembrane serine/threonine kinase receptors (8). In 1991, the Type II receptor for activin, designated ActRII, was cloned and characterized (9). ActRII was the first vertebrate receptor serine kinase (RSK) to be characterized as well as the first receptor to be described in molecular detail for any member of the TGF-β superfamily. Over a dozen receptor serine kinase family members have now been identified including a second Type II activin receptor (ActRIIB) (10,11), the Type II TGF-β receptor (12) and Type I receptors for both activin (13,14) and TGF-β (15).

The broad spectrum of critical biological actions of inhibin, activin and related factors as well as their connection to potential applications for the treatment of reproductive, developmental, bone, hepatic, hematopoietic and central nervous system disorders together form a compelling rationale for the exploration of their receptors, signaling mechanisms, and regulation. Collectively, this work involves the identification of multiple novel molecular targets and should therefore provide the basis for new therapeutic approaches aimed at treating endocrine disorders and neoplastic diseases.

Activins (β-β) and inhibins (α-β) are structurally related by virtue of a common 14-kDa β subunit while the inhibin dimer also has a dissimilar 18-kDa α subunit. Isoforms of activin and inhibin have been isolated from follicular fluid. These include activin A (βA-βA), activin B (βB-βB), activin AB (βA-βB), inhibin A (α-βA), and inhibin B (α-βB). Based on sequence alignment and locations of conserved cysteine residues, these polypeptides are thought to be structurally similar to other TGF-β family members for which crystal structure information is available (16,17).

To date, inhibin has been shown to have activity only in the context of activin responses where it typically antagonizes the activin signal (5,18–20) although there are recent reports in abstract form of activin-independent inhibin effects in bone. It has been shown that inhibin can compete with activin for binding to its target cells and that inhibin can prevent activin-induced receptor heteromerization (5,19). Unlabeled inhibin directly competes with labeled activin for binding to type II activin receptors although its potency as a displacing agent is approximately ten-fold lower than that of unlabeled activin (9,10).

The β subunits present in both activin and inhibin are proposed to mediate binding to type II activin receptors. After activin binds ActRII, the activin-ActRII complex subsequently promotes the recruitment and phosphorylation of the type I activin receptor serine kinase ALK4 (5,8,14). This results in phosphorylation of the cognate type I receptor and the activation of downstream Smad proteins (21,22). Inhibins also bind to type II activin receptors, but the α subunit of the inhibin molecule does not support the recruitment of type I receptors (i.e. ALK4). This suggests that inhibins block signaling through direct competition for receptor access (5,18,19), thus preventing activin binding to type II activin receptors (23). However, inhibins fail to antagonize activin in some tissues and cells consistent with the hypothesis that additional components are required for inhibin action (5,24,25).

Previous findings indicate that an additional receptor component may be required for inhibin to successfully compete with activin for access to the type II activin receptor and to thereby functionally antagonize activin responses. It is likely that simple, direct competition for access to the activin type II receptor between activin and inhibin is not solely sufficient to explain the effects of inhibin on activin responses. Indeed, the ability of activin to suppress pituitary ACTH secretion is not antagonized even by a large molar excess of inhibin (6). In addition, in K562 erythroleukemic cells engineered to overexpress ActRII (KAR6 cells), increased ActRII expression blocks the ability of inhibin to antagonize activin signaling even in the presence of a substantial molar excess of inhibin (5).

In an effort to identify putative inhibin-specific receptor components, cross-linking experiments were performed using [$^{125}$I]-labeled activin and inhibin to label both wild type K562 erythroleukemic cells and KAR6 cells overexpressing ActRII. The results showed that activin binds to type I and type II receptors in both cell lines and that binding of labeled activin to the two receptors was displaced by an excess of unlabeled activin or unlabeled inhibin (5). As expected, the labeled inhibin is capable of binding the type II receptor but not the type I receptor in both cell lines. Inhibin's binding to the type II receptor can be displaced by addition of either unlabeled activin or inhibin. Interestingly, a high molecular weight protein cross-linked to labeled inhibin was also evident in these experiments that could be competitively displaced by addition of excess unlabeled inhibin but not activin (5).

Together, these results suggest that in addition to binding to ActRII, inhibin also binds another putative co-receptor of higher molecular weight that might serve to stabilize the inhibin-ActRII interaction and therefore prevent ActRII from binding activin and mediating activin responses. The lack of inhibin antagonism of activin responses in certain tissues can therefore be explained by the absence of this or a similar inhibin binding co-receptor component. The presence of a similar high molecular weight inhibin-binding component in the ovarian tumor cell line KK-1 has been subsequently confirmed. High affinity inhibin binding to unidentified high molecular weight proteins has also been reported (24).

Betaglycan is the type III TGF-β receptor and was originally identified as the largest of three cell surface receptors shown to bind TGF-β with high affinity (26). The rat betaglycan cDNA encodes a protein of 853 amino acids containing a large extracellular domain, a single transmembrane domain, and a short C-terminal cytoplasmic domain that lacks clearly identifiable signaling motifs (27,28). Betaglycan binds all three TGF-β isoforms with high affinity and is thought to play an accessory role in facilitating access of TGF-β to its signaling receptors (22,29).

Mature betaglycan is a proteoglyean which contains both heparan sulfate and chondroitin sulfate glycosaminoglycan (GAG) chains yielding a molecule that migrates between 250 kDa and 350 kDa on SDS-PAGE gels. The betaglycan core polypeptide without attached glycosaminoglycan chains retains TGF-β binding activity and migrates as a protein of 100–110 kDa (27,30,31). Recent work has demonstrated the importance of betaglycan in mediating physiological responses to TGF-β including its autocrine regulation of human breast cancer cell proliferation (32,33) and its ability to trigger endocardial cell transformation (34).

The prior art is deficient in the lack of characterization of the protein mediating the interaction of inhibin with the activin receptor. The present invention fulfills this long-standing need and desire in the art.

SUMMARY OF THE INVENTION

In one embodiment of the current invention, a method is described whereby activin-induced signaling in an inhibin-sensitive cell may be augmented by inhibiting the formation of inhibin/betaglycan complexes. An antiserum may be directed against an extracellular epitope of betaglycan to prevent the binding of inhibin to betaglycan. Alternatively, the formation of inhibin/betaglycan complexes may be inhibited by reducing the expression of betaglycan in the cells by either antisense inhibition or by mutagenesis of one or both betaglycan alleles by such methods as homologous recombination. A potential application of this method is to augment activin signaling in pituitary cells. This should result in an increase in the production of Follicle Stimulating Hormone (FSH) and thus an enhancement of fertility. The method can also be applied to the treatment of a number of pathophysiological conditions including reproductive, developmental, skin, bone, hepatic, hematopoietic and central nervous system disorders such as prostrate cancer.

In another embodiment of the instant invention, an antiserum directed against the extracellular portion of betaglycan is provided. This antiserum inhibits the binding of inhibin to betaglycan and may be incorporated into a pharmaceutical composition.

In yet another embodiment of the instant invention, a method inhibiting activin-induced signaling is provided. This is accomplished by augmenting the formation of inhibin/betaglycan complexes on the surface of the target cells. One such method entails increasing the expression of betaglycan in the target cells to provide extra betaglycan for the formation of such complexes. This method can be further enhanced by the administration of additional inhibin. Betaglycan expression can be increased by transfecting the target cells with an artificial construct expressing betaglycan either constitutively or by an inducible promoter. This method may also be used to introduce inhibin sensitivity to cells not normally responsive to inhibin. A number of pathophysiological conditions including reproductive, developmental, skin, bone, hepatic, hematopoietic and central nervous system disorders may be treated in this manner. Examples include gonadal cancer, adrenal cancer, and liver dysplasia. The method may also be used to promoter liver regeneration.

Yet another embodiment of the instant invention is a method of screening for compound which inhibit the formation of inhibin/betaglycan complexes to augment activin signaling. Membranes from cells expressing betaglycan are incubated in the presence and absence of potential inhibitors of inhibin binding to betaglycan. An assay such as a competitive binding assay is performed and the results are compared. A compound which inhibits the formation of inhibin/betaglycan complexes will result in lower levels of inhibin binding. Potential compounds may peptides, proteins, or small molecules. Alternatively, the method may be applied to screen compounds which augment the formation of inhibin/betaglycan complexes and thus inhibit activin signaling. In this case, the compound should increase the binding of inhibin to the membranes.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

In FIG. 1A, HEK 293 cells were transfected using calcium phosphate precipitation (35) with ActRII-myc, betaglycan (BG), or both (ActRII+BG), as indicated. Isolated cell membranes were incubated with approximately 100 pM [$^{125}$I]-inhibin A in the presence or absence of various concentrations of unlabeled inhibin A competitor.

FIG. 1B shows the data of FIG. 1A normalized and presented as % specific binding. Binding data were analyzed using the Prism software.

In FIG. 2A, covalent crosslinking of inhibin A to ActRII is increased by betaglycan. Empty vector (pcDNA3), ActRII-myc, betaglycan (BG), or both ActRII and betaglycan (BG+ActRII-myc) were transfected into HEK 293 cells which were then subjected to crosslinking with [$^{121}$I]-inhibin A and DSS as previously described for activin (9). Binding and crosslinking of [$^{125}$I]-inhibin A to betaglycan expressing cells was performed in the presence or absence of 25 nM unlabeled inhibin A, 25 nM unlabeled activin A, or 5 nM unlabeled TGF-$β_1$ as indicated. Crosslinked complexes isolated by immunoprecipitation using anti-betaglycan antiserum (R&D Systems, Inc.) or a monoclonal anti-myc antibody (9E10) (Calbiochem, Inc.). The crosslinked proteins were resolved under reducing conditions by SDS-PAGE and visualized by autoradiography. The positions of ActRII-myc, the betaglycan core polypeptide (Core), and betaglycan containing glycosaminoglycan chains (BG) are indicated. Molecular weight markers are represented as $M_r \times 10^{-3}$.

FIG. 2B shows covalent crosslinking of inhibin A and activin A to endogenous betaglycan complexes. Binding and crosslinking of [$^{125}$I]-inhibin A and [$^{125}$I]-activin A was performed on KK-1 cells expressing endogenous receptors in the presence or absence of 25 nM unlabeled inhibin A or 25 nM unlabeled activin A, as indicated. Crosslinked complexes isolated by immunoprecipitation using anti-betaglycan antiserum (R&D Systems, Inc.), anti-ActRII antiserum or normal rabbit serum were resolved under reducing conditions by SDS-PAGE and visualized by autoradiography. The positions of ActRII, the betaglycan core polypeptide (BG Core), betaglycan containing glycosaminoglycan chains (BG) and Alk4 are indicated. Molecular weight markers are represented as $M_r \times 10^{-3}$.

In FIG. 4A, AtT20 cells were transfected with the 3TPLux-reporter plasmid (7), CMV-β-galactosidase (β-GAL) and either empty vector or betaglycan (BG) cDNA using Superfect Transfection Reagent (Qiagen) under optimized conditions. Cells were treated with or without 2.5 nM inhibin A (Inh A) and various concentrations of activin A (Act A) for 15 h and the resulting luciferase activities were measured.

In FIG. 4B, AtT20 cells were transfected, as outlined for FIG. 4A, and then treated with or without 1 nM activin A and a range of inhibin A concentrations.

In FIG. 4C, KK-1 ovarian tumor cells were transfected as described above and treated with or without 0.3 nM activin A and a range of inhibin A concentrations.

In FIG. 4D, K562-derived KAR6 cells were transfected with betaglycan (BG) or empty vector, treated with IPTG to induce activin receptor expression, and treated with 0.3 nM activin A and a range of inhibin A concentrations. Luciferase activity is represented in arbitrary luciferase units (L.U.) and normalized to β-GAL activity.

DETAILED DESCRIPTION OF THE INVENTION

Figure 1A:
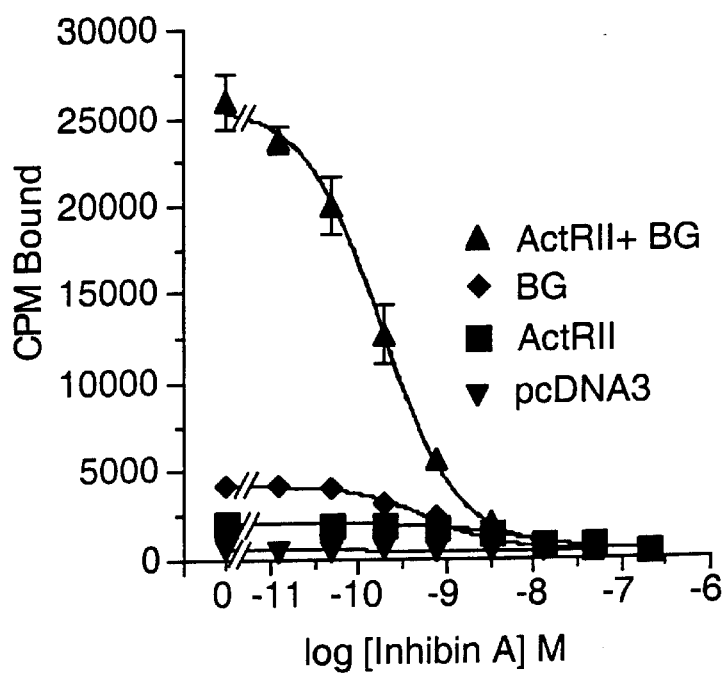
FIGS. 1A and 1B show that betaglycan binds inhibin with high affinity and increases inhibin binding to ActRII.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acids described herein are preferred to be in the "L" isomeric form. However, residues in the "D" isomeric form can be substituted for any L-amino acid residue, as long as the desired functional property of immunoglobulin binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

The labels most commonly employed for these studies are radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many such enzymes are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

The current invention is directed to a method of augmenting activin-induced signaling by inhibiting the formation of inhibin/betaglycan complexes. An antiserum against an extracellular epitope of betaglycan can be used to inhibit the formation of such complexes. Alternatively, the amount of betaglycan available for forming the complexes may be limited by reducing the expression of betaglycan in the cells. The expression of betaglycan may be reduced by anti-betaglycan antisense transcripts or by mutagenesis of one or both betaglycan alleles in the cells. Homologous recombination is one method which may be used to mutate betaglycan. Pituitary cells are a potential target of this method wherein augmentation of activin signaling increases the production of Follicle Stimulating Hormone (FSH) and enhances fertility. Alternatively, the method may be applied to the treatment of a number of reproductive, developmental, skin, bone, hepatic, hematopoietic and central nervous system disorders such as prostrate cancer.

The instant invention is also directed to the antibetaglycan antiserum which inhibits the binding of inhibin to betaglycan. The antiserum may be combined with a pharmaceutically acceptable carrier to form a pharmaceutical composition.

A method of inhibiting activin-induced signaling by enhancing the formation of inhibin/betaglycan complexes is also provided. The main method of accomplishing this is by increasing the expression of betaglycan in said cell. Additional inhibin may also be administered to promote the formation of the complexes. Expression can be enhanced by transfecting an artificial construct containing a betaglycan gene. The betaglycan gene may be either constitutively expressed or placed under the control of an inducible promoter. This method may also be used to introduce sensitivity to inhibin in cells not normally responsive to inhibin. The method may be used to treat a number of pathophysiological condition including reproductive, developmental, skin, bone, hepatic, hematopoietic and central nervous system disorders. Specific examples include the treatment of gonadal cancer, adrenal cancer, or liver dysplasia. The method can also be used to promote the regeneration of damaged liver tissue The instant invention is also directed to methods screening for compounds which inhibit formation of inhibin/betaglycan complexes and thus augment activin signaling. An assay for inhibin binding to betaglycan is performed on membranes from cells expressing betaglycan. If the compound results in a lower level of inhibin binding in membranes from cell treated with the compound than those from untreated cells, the compound inhibits the formation of inhibin/betaglycan complexes and will augment activin signaling. The method may be used to test a number of possible compounds including peptides, proteins, and small molecules. Alternatively, the method may be applied to screen compounds which augment the formation of inhibin/betaglycan complexes and thus inhibit activin signaling. In this case, the compound should increase the binding of inhibin to the membranes.

The following examples are given for the purpose of illustrating various embodiments of the invention and are not meant to limit the present invention in any fashion.

EXAMPLE 1

Competition Binding Studies

Recombinant human activin A and inhibin A were generated using a stable activin-expressing cell line provided by Dr. J. Mather (Genentech, Inc.) and were purified by Wolfgang Fischer (PBL, Salk Institute). [$^{125}$I]-Activin A and [$^{125}$I]-Inhibin A were prepared using the chloramine T method as previously described (37).

For binding studies, cells were transiently transfected using DEAE Dextran with 10 μg of ActRII and/or 10 μg of betaglycan plasmid DNA. The cells were incubated with the DNA for 4 hours, shocked with 10% DMSO in Hepes Dissociation Buffer (HDB), and incubated at 37° C. and 5% $CO_2$ for 48 hours in DMEM containing 10% fetal calf serum and L-glutamine. Confluent monolayers were washed twice with Hepes Dissociation Buffer and resuspended in binding buffer (Hepes Dissociation Buffer with 0.1% BSA, 5 mM $MgSO_4$ and 1.8 mM $CaCl_2$). Binding was carried out by incubating ~$2 \times 10^5$ cells with $2 \times 10^5$ cpm [$^{125}$I]-inhibin A (approximately 100 pM) for 90 min at room temperature in the presence or absence of various concentrations of unlabeled inhibin or activin in a final volume of 0.4 ml binding buffer. Following binding, the cells were pelleted by centrifugation and washed twice in binding buffer. Bound [$^{125}$I]-inhibin A was quantitated using a gamma counter and analysis of binding data was carried out using the Prism program.

EXAMPLE 2

Crosslinking Studies

Crosslinking studies were carried out in cells grown to ~40–60% confluence in 5% $CO_2$ in complete DMEM (with 10% bovine calf serum, penicillin, streptomycin and L-glutamine). The cells were grown in 10 cm culture dishes and then transfected using the calcium phosphate precipitation method using Hepes-buffered saline (pH 7.07). Following transfection, cells were incubated at 5% $CO_2$ for 48 hours. Cell were harvested by rinsing each plate once with Hepes Dissociation Buffer and then incubating each plate in Hepes Dissociation Buffer containing 1 mM EDTA for 10 min to release the cells.

Covalent crosslinking was carried out by incubating $10^6$ cells resuspended in Hepes Dissociation Buffer with ~$2 \times 10^6$ Cpm [$^{125}$I]-activin A in a total of 500 μl for 1 hour at room temperature with gentle rocking. Following this incubation, 1 ml cold Hepes Dissociation Buffer was added to each tube and cells were then pelleted by centrifugation, resuspended in 500 μl HDB, brought to 0.5 mM disuccinylsuberate (DSS) and incubated 30 min on ice. Each reaction was quenched by adding 1 ml TBS to each tube. The cells were then pelleted by centrifugation, aspirated, and pellets solubilized in 1 ml lysis buffer (20 mM Tris-HCl pH 7.5, 0.2 mM EDTA, 1% Triton X-100, 1 mM AEBSF, 1 mM EDTA, 10 μg/ml leupeptin, 10 μg/ml pepstatin, and 1 μg/ml aprotinin) on ice for 30 min. TX-100-insoluble material was removed by centrifugation, and 2 μg anti-betaglycan or 2 μg anti-myc antibody was added to each supernatant. Tubes were incubated for 16 hours at 4° C., and immune complexes were precipitated by adding 10 μl of 50% protein G agarose (PGA) slurry to each tube, incubating an additional 1 hour at 4° C., and pelleting immobilized immune complexes by centrifugation. Each protein G agarose pellet was washed three times with 1 ml lysis buffer and then boiled 10 min, eluted in 25 μl SDS sample buffer and resolved via SDS-PAGE. All SDS-PAGE was carried out under reducing conditions on polyacrylamide 3–8% Tris-Acetate NuPAGE gels (Novex). Gels were dried and bands were detected via autoradiography.

EXAMPLE 3

Luciferase Assays in AtT20 and KK-1 Cells

The function of betaglycan was evaluated in transient transfection experiments using a well-characterized activin/TGF-β-responsive luciferase reporter plasmid, 3TPLux (14). Two mouse cell lines were tested; AtT20 corticotropic cells (grown in DMEM, 10% FBS, 2 mM L-glutamine and gentamycin) and KK-1 ovarian cells (grown in DMEM:F12 with 10% FBS, L-glutamine, penicillin and streptomycin). The cells were trypsinized and plated at a density of 1.5–2× $10^5$ cells/well in 6-well plates 24 hours before transfection. The cells were transfected in complete medium with approximately 1 μg of 3TPLux, 0.1–0.2 μg cytomegalovirus (CMV)-β-galactosidase (β-GAL) and 0.1–0.3 μg of either vector or betaglycan plasmid DNA. Transfections were under optimized conditions using the commercially available Superfect Transfection Reagent (Qiagen; Hilden, Germany). After an incubation period of 2.5 h, the cells were washed with medium containing 2% FBS and allowed to recover for 5 hours. The cells were treated with inhibin A and/or activin A for 15 hours and then harvested in lysis buffer (1% Triton X-100, 25 mM Glycylglycine (pH 7.8), 15 mM $MgSO_{4,}$ 4 mM EGTA and 1 mM DTT). Luciferase reporter activity was determined by normalizing to relative β-GAL activities.

EXAMPLE 4

Immunocytochemistry

Normal adult male and female sprague-dawley rats (175–250 g; Harlan Sprague Dawley) were kept under standard housing, feeding, and lighting conditions (23° C., 12 hours light, 12 hours dark cycle with lights on at 0600 h). Immunocytochemistry (ICC) was carried out as previously described (MacConell et al., 1998). Briefly, rats were deeply anesthetized and perfused transcardially with 4% paraformaldehyde. Tissues (brain, pituitary, testes or ovaries) were removed and post-fixed for 1 hour in the same fixative. Brains were transferred to 10% sucrose/0.02 M potassium phosphate buffered-saline (KPBS) and stored overnight at 4° C. Thirty μm frozen coronal sections were cut on a sliding microtome and free-floating sections processed for ICC analysis as described below. Pituitary, testis and ovary tissues were embedded in paraffin and 10 μm paraffin sections were cut, mounted onto Superfrost Plus slides (Fisher Scientific), and processed for ICC analysis. All procedures involving the use of animals were performed in accordance with federal, state, and local laws and institutional and NIH regulations.

To reduce background staining, tissue sections were incubated for 20 min in 1% $H_2O_2$ and rinsed with KPBS followed by a 1 hour room temperature incubation in KPBS with 0.3% Triton X-100, 10% normal rabbit serum, and 2% BSA. Sections were incubated with betaglycan primary antisera (R&D) at a concentration of 25 µg/ml in KPBS plus 0.3% Triton-X, 2% normal rabbit serum, and 2% BSA overnight at 4° C. (as a control, adjacent sections were incubated with normal goat IgG or secondary antibody alone). Tissue sections were then rinsed in KPBS followed by an 1 hour incubation with a 1:1,000 dilution of biotinylated rabbit anti-goat secondary (Vector) at room temperature. KPBS-washed tissue was incubated in an avidin-biotin-horseradish peroxidase complex (Vector) for 1 hour at room temperature. The peroxidase reaction was then visualized as a brown reaction product with a 3–5 min incubation in a mixture of 0.03% DAB and 0.015% $H_2O_2$ in 0.1M Tris-HCl, pH 7.4. The free-floating brain sections were mounted onto Superfrost/Plus slides (Fisher Scientific) and light microscopy employed for visualization of immunoreactivity.

EXAMPLE 5
Betaglycan Binds Inhibin with High Affinity and Increases Inhibin Binding to ActRII In the process of screening for potential inhibin binding proteins, inhibin binding was detected in cells expressing betaglycan. FIG. 1 shows that isolated membranes from HEK 293 cells transfected with betaglycan exhibited specific, high affinity inhibin binding [Ki=0.6 (0.5–0.9) nM] whereas membranes from cells transfected with empty vector had undetectable specific inhibin binding.

Figure 1B:
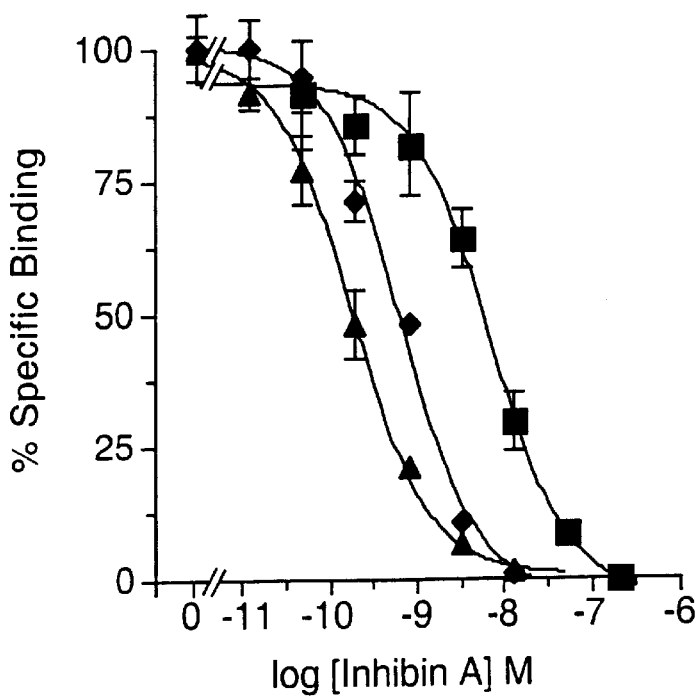

To further characterize inhibin binding in isolated membranes from cells expressing ActRII or co-expressing ActRII and betaglycan, cDNAs encoding these receptors were transfected into HEK 293 cells and competition binding assays were performed. The inhibin binding affinity was quite low when ActRII was expressed alone [Ki=6.3 nM (2.9–13.4) nM], consistent with previous results (9), but increased approximately 30-fold when ActRII and betaglycan were co-expressed [Ki=0.2 (0.1–0.3) nM] (FIG. 1B). Moreover, co-expression of ActRII and betaglycan increased the number of inhibin binding sites approximately twelve-fold or six-fold relative to the number of binding sites in cells expressing ActRII or betaglycan alone, respectively FIG. 1A). Experiments performed with betaglycan and ActRIIB had similar results; however, the effects of betaglycan on increasing inhibin affinity and the number of inhibin binding sites were less dramatic (data not shown). Activin binding to betaglycan was not detected during expression in HEK 293 cells. Also, betaglycan did not increase binding of activin to ActRII (data not shown), indicating that betaglycan did not increase inhibin binding by means of increasing ActRII expression.

EXAMPLE 6
Covalent Crosslinking of Inhibin to Betaglycan and Covalent Crosslinking of Inhibin to the ActRII-betaglycan Complex To determine whether inhibin is capable of binding and forming a complex with betaglycan expressed either with or without ActRII, both receptors were expressed in HEK 293 cells. The cells were treated with [$^{125}$I]-inhibin followed by the covalent crosslinking reagent disuccinylsuberate (DSS). Crosslinked inhibin-receptor complexes were then immunoprecipitated with an antibody directed against either the ActRII myc epitope of the extracellular domain of betaglycan. The crosslinked, immunoprecipitated complexes were resolved by SDS-PAGE and visualized by autoradiography.

Figure 2A:
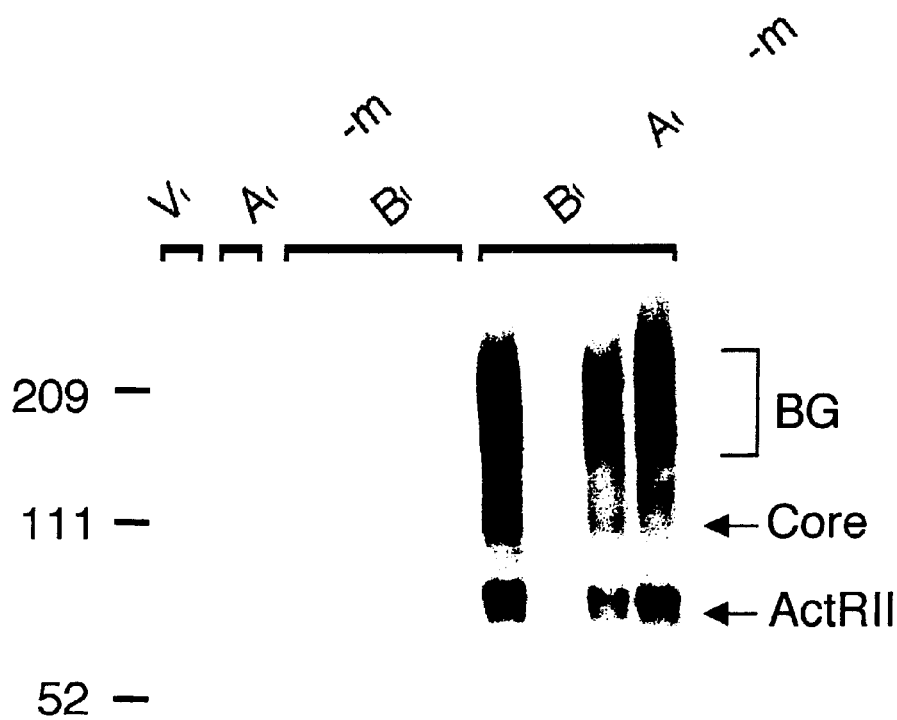
FIGS. 2A and 2B illustrate covalent crosslinking of inhibin to betaglycan (transfected and endogenous) and provide evidence for an ActRII-betaglycan complex.

FIG. 2A shows the results of such a crosslinking experiment in which cells were transfected with either vector alone (lane 1), ActRII alone (lane 2), betaglycan alone (lanes 3–6), or betaglycan and ActRII together (lanes 7–10). Crosslinking with [$^{125}$I]inhibin did not yield any visible complexes on SDS-PAGE analysis in cells transfected with empty vector (FIG. 2A, lane 1). A covalent complex of approximately 75–85 kDa was detected in cells transfected with ActRII alone (FIG. 2A, lane 2), a size consistent with previously reported crosslinked complexes of inhibin/activin-ActRII (8,9,18,19). Crosslinking of [$^{125}$I]-inhibin to cells transfected with betaglycan alone yielded a complex at approximately 110 kDa and another diffuse band at 175–250 kDa (FIG. 2A, lane 3). Previous experiments with [$^{125}$I]-TGF-β crosslinked to betaglycan have demonstrated complexes with similar mobility (27,28) representing the betaglycan core protein (~110 kDa) and betaglycan with glycosaminoglycan chains (200–300 kDa). Therefore, the bands seen following inhibin labeling contain the predicted forms of betaglycan.

Similar high molecular weight inhibin complexes of the same size range as those present in cells expressing betaglycan have been previously reported (5,24,38). The addition of 25 nM unlabeled inhibin or 5 nM unlabeled TGF-β prevented crosslinking of inhibin to betaglycan (FIG. 2A, lanes 4 and 6). By contrast, 25 nM unlabeled activin had no effect (FIG. 2A, lane 5). These results are consistent with activin's lack of affinity for this proteoglycan and the possibility that betaglycan binds the α subunit of inhibin. The ability of TGF-β to block inhibin crosslinking indicates that the binding site for inhibin overlaps with at least one of the TGF-β binding sites on betaglycan.

When ActRII and betaglycan were co-expressed, the levels of inhibin-crosslinked receptor complexes were dramatically increased and covalent complexes between [$^{125}$I]-inhibin and both ActRII and betaglycan were evident (FIG. 2A, lane 7). Inhibin-labeled complexes in the expected size range for betaglycan were co-immunoprecipitated with an anti-myc antibody directed against ActRII (FIG. 2A, lane 7), providing evidence that inhibin, ActRII and betaglycan interact to form an oligomeric inhibin receptor complex. The presence of 25 nM unlabeled inhibin completely blocked [$^{125}$I]-inhibin labeling of both ActRII and betaglycan in cells expressing both receptors (FIG. 2A, lane 8). By contrast, the addition of 25 nM activin or 5 nM TGF-β had little effect on the intensity of the bands that were labeled with [$^{125}$I]-inhibin (FIG. 2A, lanes 9 and 10). The inability of unlabeled TGF-β to block inhibin crosslinking to betaglycan co-expressed with ActRII is consistent with the presence of an ActRII/betaglycan complex that binds inhibin but not TGF-β.

Figure 2B:
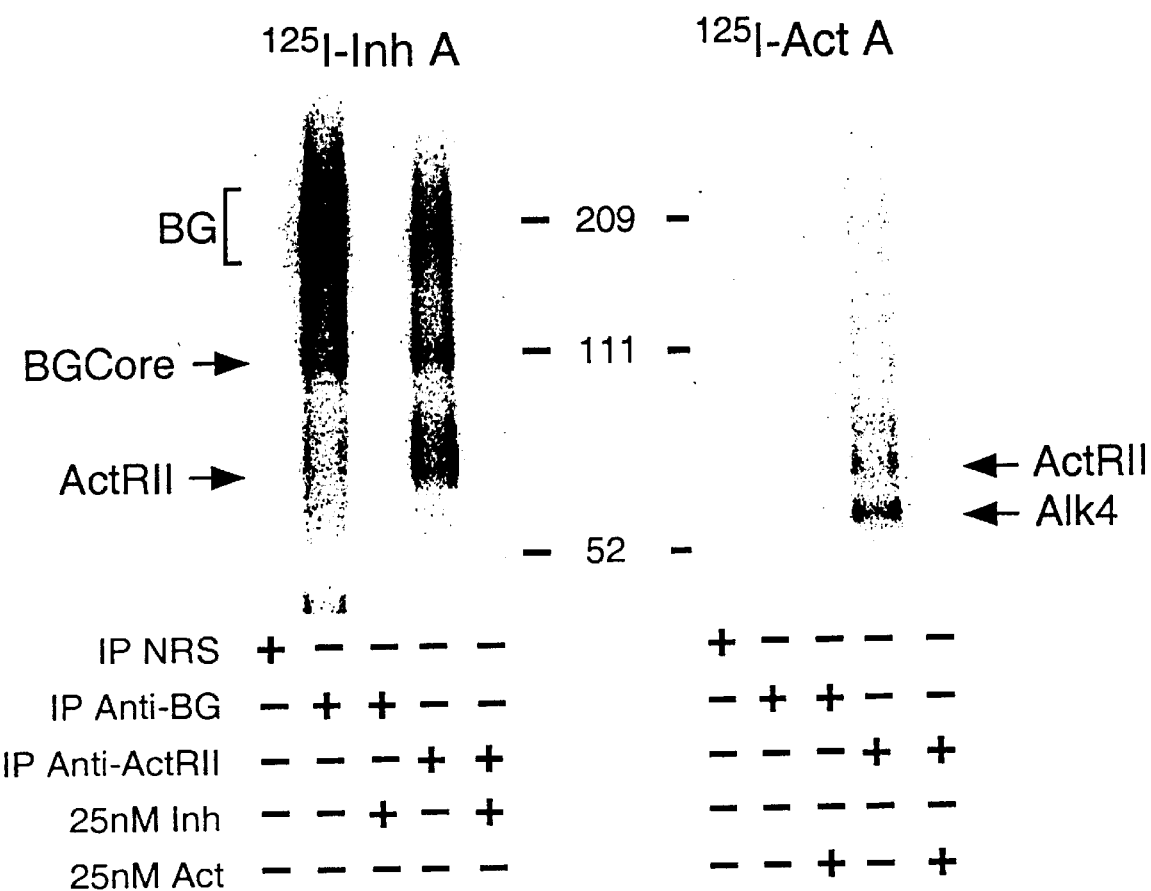

In addition to its ability to form a crosslinked complex with recombinant betaglycan and ActRII in transfected cells, inhibin also binds and forms crosslinked complexes with endogenous betaglycan and ActRII in the ovarian mouse cell line KK-1 (FIG. 2B) (38). These complexes can be visualized following immunoprecipitation with either anti-betaglycan antiserum (lane 2) or anti-ActRII antiserum (lane 4). The formation of labeled complexes is blocked by incubating with an excess of unlabeled inhibin A (FIG. 2B). Immunoprecipitated complexes include the betaglycan core protein, betaglycan with glycosaminoglycan chains, and ActRII while the activin type I receptor Alk4 is not present in the complex (FIG. 2B). Labeling of KK-1 cells with $^{125}$I-activin followed by crosslinking and immunoprecipitation with anti-betaglycan antibody demonstrates that endogenous betaglycan does not form a covalent complex with activin (lanes 7 and 9). When activin-crosslinked cells are immunoprecipitated with anti-ActRII antibody, ActRII and Alk4, but not betaglycan, are visualized (lane 9).

EXAMPLE 7

Expression of Betaglycan in Inhibin-responsive Tissues

Substantial evidence implicates inhibin as an important paracrine/autocrine regulator of the hypothalamic-pituitary-gonadal axis (39). Therefore, immunocytochemistry was employed to assess whether the tissue-specific distribution of betaglycan protein matches that of tissues documented to be inhibin-responsive. Surprisingly, despite the fact that betaglycan has been known as a TGF-β receptor for quite some time, the tissue distribution of betaglycan in vivo remains largely unexplored. The immunocytochemical localization of betaglycan in the normal adult rat brain, pituitary, ovary, and testis is summarized in FIG. 3.

Perhaps the best known function of inhibin is its selective inhibition of anterior pituitary FSH secretion (1,40–42). As shown in FIG. 3B, consistent with a role of betaglycan in mediating the inhibin response, strong betaglycan-ir was observed in a subset of cells throughout the anterior lobe of the normal adult male rat pituitary gland, exhibiting a predominantly cytoplasmic localization. These betaglycan-immunopositive cell types within the anterior pituitary may represent gonadotropes and lactotropes as these pituitary cell types are major inhibin- and TGF-β-targets, respectively (43–45). Interestingly, intense betaglycan-ir was also found in a majority of cells within the intermediate lobe of the pituitary (FIG. 3C). While an inhibin effect on cells within this lobe has not been documented, TGF-$β_1$ has been reported to co-localize with the melanotropes of the intermediate lobe, indicating it may play a role in regulation of this cell type (46). Positive immunostaining for betaglycan was not detected in the posterior lobe of the pituitary (FIG. 3C).

Figure 3A:
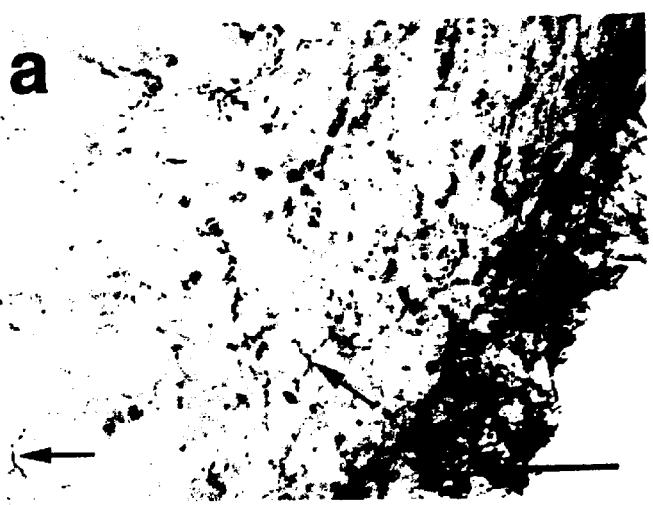
FIGS. 3A–3F show immunocytochemical localization of betaglycan in normal adult rat brain, pituitary, ovary, and testis. High magnification bright-field photomicrographs show betaglycan immunostaining in the forebrain (FIG. 3A), pituitary (FIGS. 3B and 3C), epididymis (FIG. 3D), testis (FIG. 3E), and ovary (FIG. 3F). Typical examples of cells immunopositive for betaglycan (brown staining) are indicated by the arrows. Bars depict 50 μm. Abbreviations include: AL, anterior pituitary lobe; CT, connective tissue; GC, Granulosa cells; IL, intermediate pituitary lobe; LC, leydig cells; O, oocyte; PL, posterior pituitary lobe; ST, seminiferous tubule; TT, Tenia Tecta; TC, theca cells.
Figure 3B:
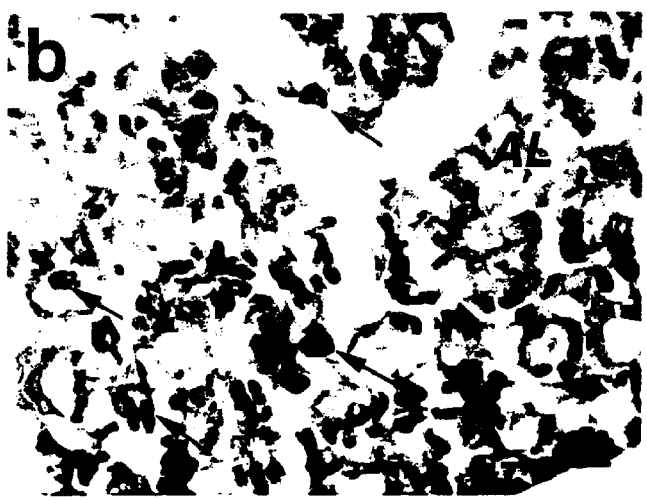
Figure 3C:
Figure 3D:
Figure 3E:
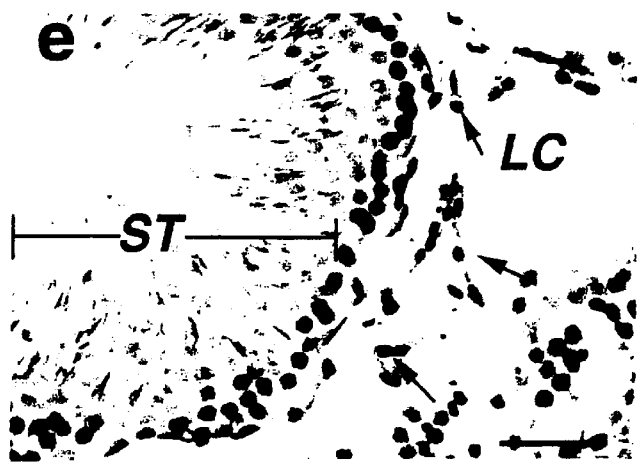

Within the testes, moderate betaglycan immunostaining is observed in the rat Leydig cells with no discernible staining for betaglycan within either Sertoli or germ cells visible at any stage (FIG. 3D). In addition, the interstitium of the epididymis stained positive for betaglycan (FIG. 3E). The immunolocalization of betaglycan to Leydig cells is consistent with the fact that inhibin, secreted by testicular Sertoli cells, acts locally to modulate steroidogenesis in Leydig cells (47,48) and the fact that inhibin-specific binding sites have been localized to this cell type (49). However, the lack of staining on germ cells was somewhat unexpected based on reported effects of inhibin on gametogenesis (50,51).

Figure 3F:
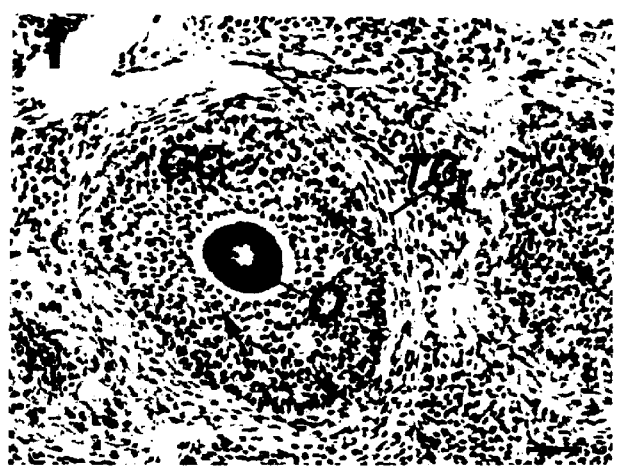

Positive immunostaining for betaglycan in the ovary was observed in granulosa, thecal, and interstitial cells of the (FIG. 3F). Like the findings in the testis, this localization is coincident with documented inhibin effects on androgen production by rat thecal cells (47).

Within the adult male rat brain, betaglycan-immunoreactive (ir) fibers were observed in the tenia tecta of the forebrain, (FIG. 3A). Betaglycan-ir fibers were also detected in the septal hippocampal nucleus of the rat forebrain (data not shown). Notably, this central localization of betaglycan in the tenia tecta corresponds with the presence of inhibin/activin α- and β-subunit mRNAs in this same region (52). Therefore, it is possible that mature inhibin secreted in this brain region interacts with similarly localized betaglycan. While the α, βA, and βB subunit proteins and mRNAs are widely distributed throughout the rostro-caudal extent of the rat brain (albeit at low levels), detection of betaglycan-ir fibers was limited to these two brain regions and perikaryal staining for betaglycan was not observed in any area of the rat brain. It is possible that expression of betaglycan in other brain regions may be below the detection level of immunocytochemistry due to low translation, rapid protein degradation, or rapid transport of the protein, indicating that colchicine treatment of rats may be necessary to visualize cell bodies immunopositive for betaglycan. It is also possible that related inhibin receptor components distinct from betaglycan are expressed in these regions performing a function similar to that of betaglycan to mediate inhibin responses.

EXAMPLE 8

Betaglycan Mediates Functional Antagonism of Activin Signaling in Corticotrope and Ovarian Cell Lines While many activin responses are potently blocked by inhibin, there are also cases in which inhibin has no measurable effect on the activin response (5,6,53,54). It has been shown in K562 erythroleukemic cells overexpressing ActRII, for example, that activin-mediated induction of the 3TPLux reporter plasmid is unaffected by the addition of high concentrations of inhibin (5). The ability of activin A to suppress basal ACTH secretion in the corticotrope cell line AtT20 has been previously described where inhibin was similarly found to have no effect on the activin response (6).

To directly test whether betaglycan can mediate the ability of inhibin to block activin signaling, the rat betaglycan cDNA and the 3TPLux reporter plasmid were transfected into AtT20 cells to determine whether betaglycan can confer inhibin responsiveness to these cells. Following transfection, the resulting ability of inhibin to block activin induction of luciferase was measured.

Figure 4A:
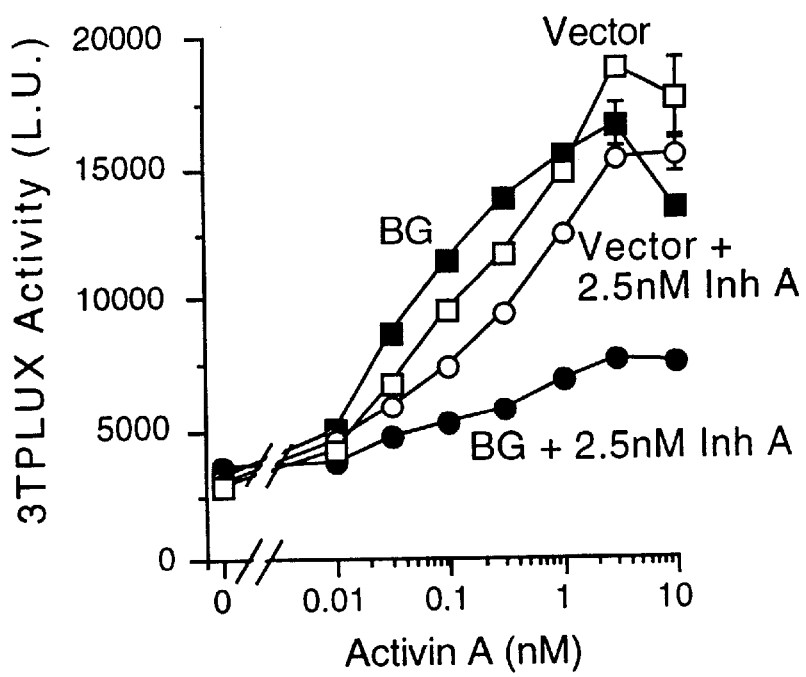
FIGS. 4A–4D show that betaglycan can mediate functional antagonism of activin signaling in corticotrope, ovarian, and erythroleukemic cells.

FIG. 4A shows that when AtT20 cells are co-transfected with either empty 3TPLux vector or 3TPLux vector expressing the betaglycan cDNA, increasing concentrations of activin A result in a dose-dependent increase in 3TPLux activity. However, when the cells are additionally treated with 2.5 nM inhibin, the activin response in betaglycan-transfected cells is substantially decreased while the activin response in cells transfected with empty vector is unaffected by inhibin (FIG. 4A).

Figure 4B:
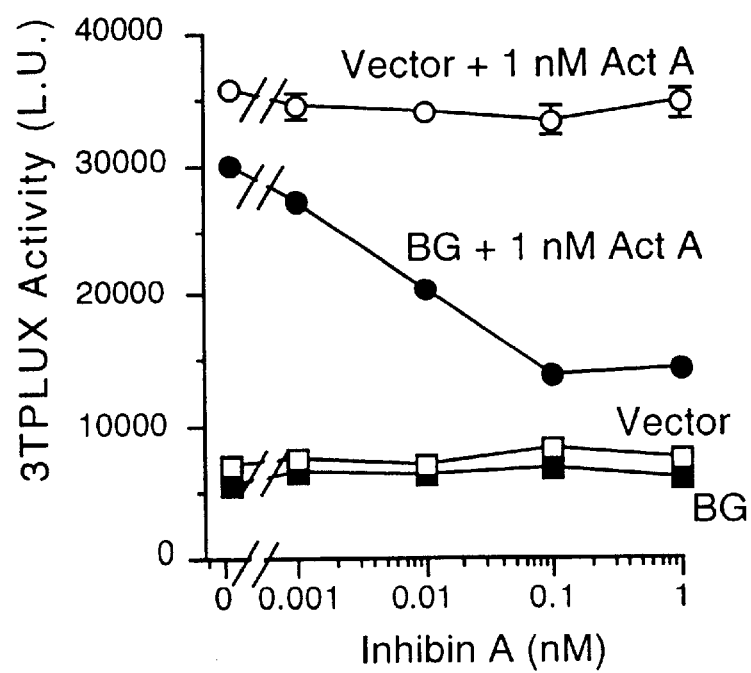

To measure the dose-dependency of this betaglycan-mediated inhibin effect, cells were again transfected with empty vector or 3TPLux plasmid containing betaglycan. The transfected cells were treated with a range of concentrations of inhibin A (FIG. 4B) in both the presence and absence of 1 nM activin A. As shown in FIG. 4B, the ability of inhibin to block activin induction of 3TPLux is dose-dependent and requires betaglycan. The effect of inhibin in cells expressing betaglycan was concentration-dependent with an estimated IC50 of 8–10 pM inhibin (FIG. 4B).

Figure 4C:
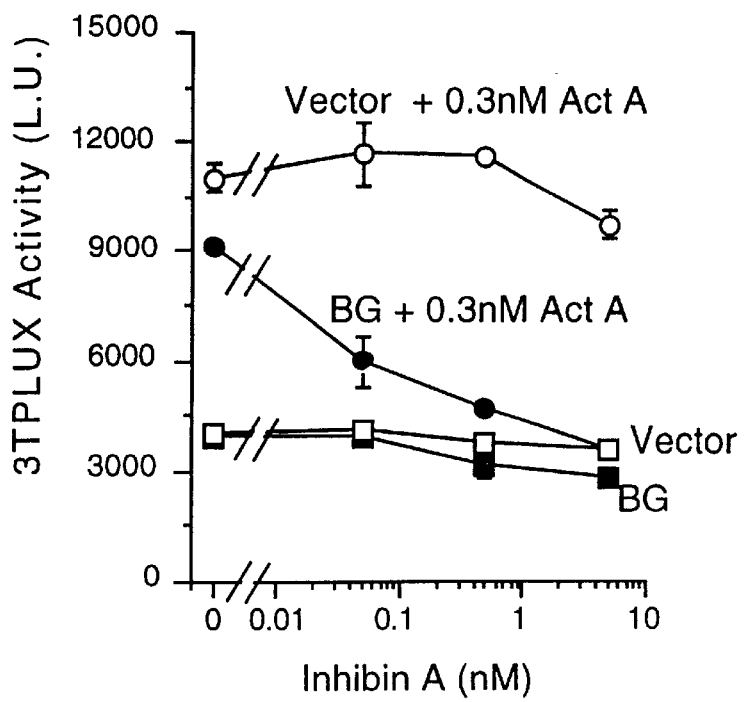
Figure 4D:
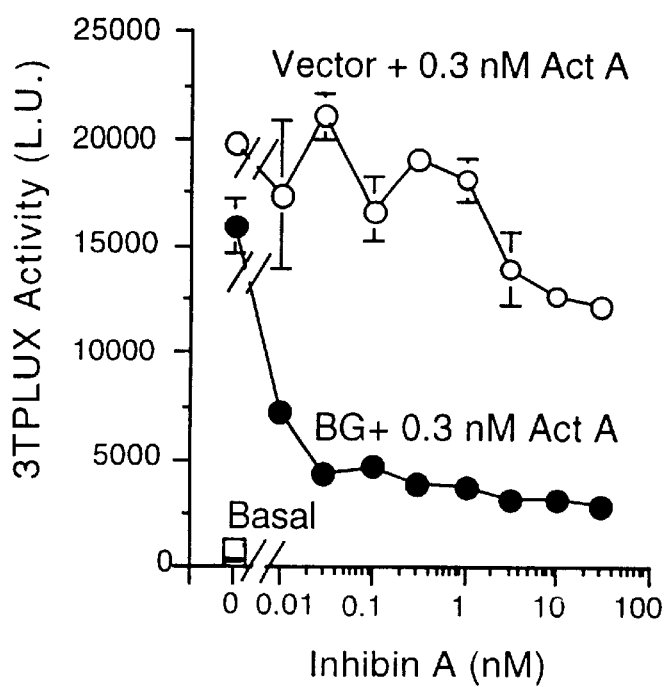

The effects of betaglycan on the inhibin responsiveness of two additional cell lines were also tested. While it was found that the ovarian cell line KK-1 is weakly inhibin-responsive (data not shown), KK-1 cells transfected with betaglycan cDNA became highly sensitive to inhibin. Activin-induced 3TPLux activity was blocked by co-treatment with inhibin (FIG. 4C). In K562 erythroleukemic cells overexpressing activin receptors (KAR6), activin-mediated induction of the 3TPLux reporter plasmid is largely unaffected by the addition of high concentrations of inhibin (5). FIG. 4D shows that KAR6 cells also displayed an inhibin-dependent reduction of activin-induced luciferase reporter activity following transfection with betaglycan cDNA but not following transfection with empty vector.

Together with the binding and crosslinking results, these results further support a model in which betaglycan acts as an inhibin receptor to facilitate inhibin binding to ActRII thereby restricting the access of activin to ActRII and antagonizing activin signaling. It is noteworthy that although the estimated affinity of inhibin for betaglycan/ActRII was ~200 pM, the range of $IC_{50}$ values (5–50 pM) for inhibin responses of the three cell types tested in the functional experiments was much lower. In some experiments, over-expression of betaglycan variably suppressed activin-induced reporter activity in the absence of added inhibin, suggesting that betaglycan might interact with ActRII in the absence of inhibin to interfere with activin signaling. It cannot be ruled out that it is possible that the inhibin/ActRII/betaglycan complex might also initiate novel signals that are distinct from those induced by activin to generate inhibin responses that are independent of activin or its receptor complex.

EXAMPLE 9
Anti-betaglycan Antiserum Experiments

Figure 5:
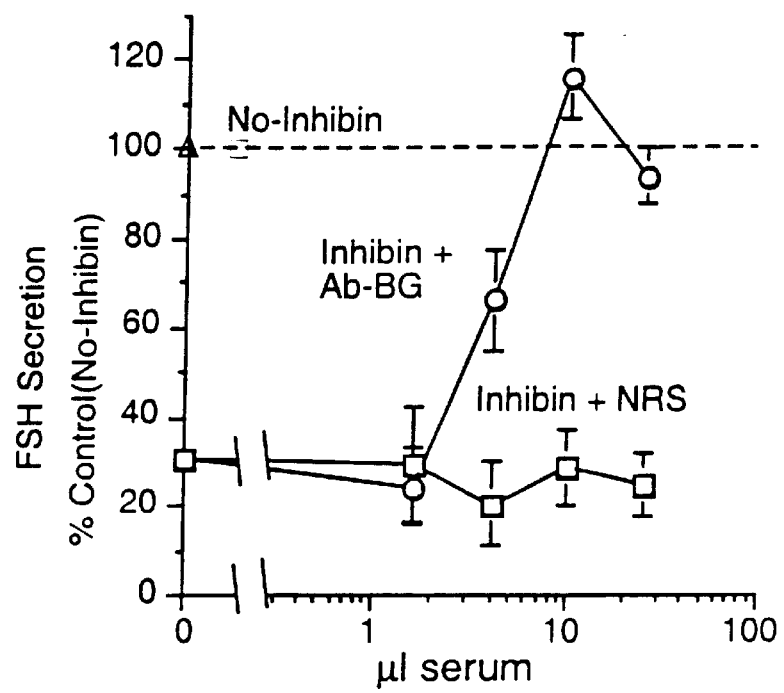
FIG. 5 demonstrates that inhibition of FSH secretion from rat anterior pituitary cells by inhibin A is blocked in a dose dependent manner in the presence of anti-betaglycan serum. Rat anterior pituitary cells were dissociated and plated as described (40). Four days after plating, the cells were washed and incubated 24 hours in 0.2% FBS-bPJ (36). The cells were then washed with fresh medium and treated with either normal rabbit serum (NRS) or antiserum from a rabbit injected with GST fusion protein to rat betaglycan residues 154–439 (Ab-BG). After 1 hour, the cells were treated with or without 25 pM of inhibin A and incubated 48 hr. FSH was measured using a radioimmunoassay kit (National Hormone and Pituitary Program of NIADDK). Reported values are represented as the percent of no inhibin treatment +/−SEM for triplicate wells.

To study the possible physiologic importance of endogenous betaglycan in mediating inhibin action, antibodies were raised against a portion of the extracellular domain of betaglycan, and the effect of these antibodies on the biological response to inhibin was examined. Anti-betaglycan antiserum (Ab-BG) was raised in rabbits against a sequence previously reported to yield antibodies capable of blocking betaglycan-dependent TGF-β signaling (34). FIG. 5 shows that inhibin reduces FSH secretion to approximately 30% of that measured for control or normal rabbit serum (NRS) treated cells. Addition of Ab-BG reverses this inhibin effect in a dose-dependent manner while normal rabbit serum (NRS) added at equivalent doses had no effect. These data indicate that betaglycan immunoneutralization inhibits the ability of inhibin to suppress FSH secretion from primary pituitary cells. This supports the hypothesis that betaglycan or an immunologically related protein is involved in the action of inhibin on the pituitary.

Figure 6:
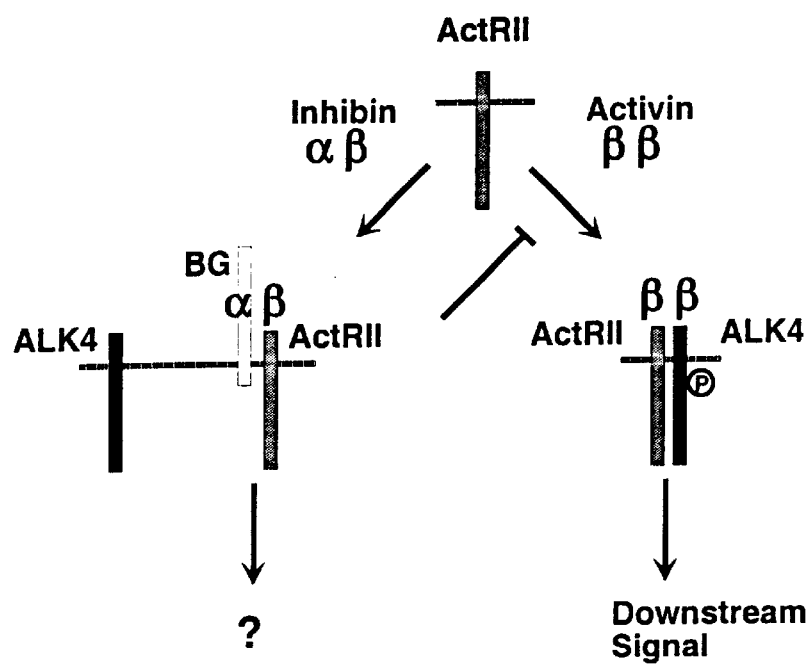
FIG. 6 is a schematic illustrating the proposed model in which betaglycan (BG) functions as an inhibin co-receptor. The presence of betaglycan or a functionally similar inhibin co-receptor increases inhibin binding to ActRII and may thereby prevent access of activin to ActRII. In addition to blocking the activin signaling pathway, the formation of the inhibin/betaglycan/ActRII complex may direct novel downstream signals.

EXAMPLE 10
A Possible Model for Inhibin Interactions with Betaglycan and ActRII Several growth factors and cytokines require cell surface proteoglycans to gain access to their respective signaling receptors and to exert biological responses (55). The data presented here are consistent with a model (FIG. 6) in which the inhibin/betaglycan complex competes with activin for access to ActRII. This may therefore prevent the formation of the activin/ActRII complex that is required for the subsequent recruitment of ALK4 and the initiation of the activin signaling cascade. This model is similar in mechanism, but not in consequence, to that proposed for TGF-β signaling in which betaglycan is thought to concentrate TGF-β at the cell surface and present it to its cognate type II receptors to enhance signaling (56). The role recently proposed for the proteoglycan mahogany to facilitate binding of the MSH antagonist, agouti, to the MSH receptor (57,58) may be the most analogous to the effects of betaglycan on inhibin action reported here.

The following references were cited herein:
1. Vale et al., 1988 Chemical and biological characterization of the inhibin family of protein hormones. In: Laurentian Hormone Conference 1988 Clark J H (ed) Recent Progress in Hormone Research, Academic Press, Inc., San Diego. vol 44, 1–34
2. Vale et al., 1998 Activins, inhibins and the receptor serine kinase superfamily and Smad proteins. In: IVth Sapporo International Symposium on Ovarian Function Sapporo, Japan 1998 Aug. 7–8, 1998
3. Kessler DaM, D A 1994 Vertebrate embryonic induction: mesodermal and neural patterning. Science 266:596–604
4. Vale W, Rivier C 1995 Activin and inhibin. In: Munson P (ed) Principles of Pharmacology: Basic Concepts & Clinical Applications. Chapman & Hall, New York, 883–886
5. Lebrun J-J, Vale W W 1997 Activin and inhibin have antagonistic effects on ligand-dependent heterodimerization of the type I and type II activin receptors and human erythroid differentiation. Mol Cell Biol 17:1682–1691
6. Bilezikjian et al., 1991 Activin-A inhibits proopiomelanocortin messenger RNA accumulation and adrenocorticotropin secretion of AtT20 cells. Mol Endocrinol 5:1389–1395
7. Massague J 1990 The transforming growth factor-b family. Annu Rev Cell Biol 6:597–641
8. Attisano et al., 1996 Activation of signaling by the activin receptor complex. Mol Cell Biol 16:1066–1073
9. Mathews L S, Vale W W 1991 Expression cloning of an activin receptor, a predicted transmembrane serine kinase. Cell 65:973–982
10. Mathews et al., 1992 Cloning of a second type of activin receptor and functional characterization in Xenopus embryos. Science 255:1702–1705
11. Attisano et al., 1992 Novel activin receptors: distinct genes and alternative mRNA splicing generate a repertoire of serine/threonine kinase receptors. Cell 68:97–108
12. Lin et al., 1992 Expression cloning of the TGF-beta type II receptor, a functional transmembrane serine/threonine kinase. Cell 68:775–785
13. ten Dijke et al., 1993 Activin receptor-like kinases: a novel subclass of cell-surface receptors with predicted serine/threonine kinase activity. Oncogene 8:2879–2887
14. Carcamo et al., 1994 Type I receptors specify growth-inhibitory and transcriptional responses to transforming growth factor beta and activin. Mol Cell Biol 14:3810–3821
15. Yamashita et al., 1994 Formation of hetero-oligomeric complexes of type i and type II receptors for transforming growth factor-beta. J Biol Chem 269:20172–20178
16. Daopin S et al., 1992 Crystal structure of transforming growth factor-beta 2: an unusual fold for the superfamily. Science 257:369–373
17. Griffith D L et al., 1996 Three-dimensional structure of recombinant human osteogenic protein 1: structural paradigm for the transforming growth factor beta superfamily. Proc Natl Acad Sci USA 93:878–883.
18. Martens et al., 1997 Inhibin interferes with activin signaling at the level of the activin receptor complex in Chinese hamster ovary cells. Endocrinology 138:2928–36
19. Xu et al., 1995 Inhibin antagonizes inhibition of liver cell growth by activin by a dominant-negative mechanism. J Biol Chem 270:6308–6313
20. Yu et al., 1987 The role of FSH releasing protein and inhibin in erythrodifferentiation. Nature 330:765–767
21. Derynck R, Zhang Y, Feng X H 1998 Smads: transcriptional activators of TGF-beta responses. Cell 95:737–740
22. Massague J 1998 TGF-beta signal transduction. Annu Rev Biochem 67:753–91
23. Xu et al., 1995 A dominant negative bone morphogenetic protein 4 receptor causes neuralization in Xenopus ectoderm. Biochem Biophys Res Commun 212:212–9
24. Woodruff T 1998 Identification of an Inhibin Receptor in Gonadal Tumors from Inhibin a-Subunit Knockout Mice. Journal of Biological Chemistry 273:398–403
25. Hertan, R., et al., 1999 Identification of high affinity binding sites for inhibin on ovine pituitary cells in culture. Endocrinology 140, 6–12

26. Massague J, Like B 1985 Cellular receptors for type beta transforming growth factor. J Biol Chem 260:2636–2645
27. Lopez-Casillas et al., 1991 Structure and expression of the membrane proteoglycan betaglycan, a component of the TGF-beta receptor system. Cell 67:785–95
28. Wang et al., 1991 Expression cloning and characterization of the TGF-beta type III receptor. Cell 67:797–805
29. Derynck R, Feng X H 1997 TGF-beta receptor signaling. Biochim Biophys Acta 1333:F105–50
30. Wang et al., 1991 Expression cloning and characterization of the TGF-beta type III receptor. Cell 67:797–805
31. Lopez-Casillas et al., Betaglycan can act as a dual modulator of TGF-beta access to signaling receptors: mapping of ligand binding and GAG attachment sites. J Cell Biol 124:557–68
32. Sun L, Chen C 1997 Expression of transforming growth factor beta type III receptor suppresses tumorigenicity of human breast cancer MDA-MB-231 cells. J Biol Chem 272:25367–72
33. Chen C, Wang X F, Sun L 1997 Expression of transforming growth factor beta (TGFbeta) type III receptor restores autocrine TGFbeta1 activity in human breast cancer MCF-7 cells. J Biol Chem 272:12862–7
34. Brown et al., 1999 Requirement of type III TGF-beta receptor for endocardial cell transformation in the heart. Science 283:2080–2
35. Chen C, Okayama H, 1987 High-Efficiency Transformation of Mammalian Cells by Plasmid DNA. Mol. Cell Biol. 7:2745–2752
36. Vale W, et al., 1983 In: Methods in Enzymology: Neuroendocrine Peptides. Conn P M, (ed.) Academic Press, New York, pp. 565–577
37. Vaughan et al., 1992 α2-macroglobulin is a binding protein of inhibin and activin. Endocrinology 132:2038–2050
38. Kananen K et al., 1995 Gonadal tumorigenesis in transgenic mice bearing the mouse inhibin alpha-subunit promoter/Simian virus t-antigen fusion gene: characterization of ovarian tumors and establishment of gonadotropin-responsive granulosa cell lines. Molecular Endocrinology, 9:616–627
39. Vale et al., 1990 The inhibin/activin family of growth factors. In: Sporn et al., (ed) Peptide Growth Factors and Their Receptors, Handbook of Experimental Pharmacology. Springer-Verlag, Heidelberg, vol 95/II, 211–248
40. Mason et al., 1985 Complementary DNA sequences of ovarian follicular fluid inhibin show precursor structure and homology with transforming growth factor-beta. Nature 318:659–663
41. Mason et al., 1986 Structure of two human ovarian inhibins. Biochem Biophys Res Commun 135:957–64
42. Mayo et al., 1986 Inhibin a-subunit cDNAs from porcine ovary and human placenta. Proc Natl Acad Sci USA 83:5849–5853
43. Carroll et al., 1989 Inhibin, activin and follistatin: regulation of follicle-stimulating hormone messenger ribonucleic acid levels. Mol Endocrinol 3:1969–1976
44. Sarkar D K, Kim K H, Minami S 1992 Transforming growth factor-b1 messenger RNA and protein expression in the pituitary gland—its action on prolactin secretion and lactotropic growth. Mol Endocrinol 6:1825–1833
45. Sarkar et al., 1998 Role of transforming growth factor (TGF)-beta Type I and TGF-beta type II receptors in the TGF-beta1-regulated gene expression in pituitary prolactin-secreting lactotropes. Endocrinology 139:3620–8
46. Burns G, Sarkar D K 1993 Transforming growth factor beta 1-like immunoreactivity in the pituitary gland of the rat: effect of estrogen. Endocrinology 133:1444–9
47. Hsueh et al., 1987 Heterodimers and homodimers of inhibin subunits have different paracrine action in the modulation of luteinizing hormone-stimulated androgen biosynthesis. Proc Natl Acad Sci USA 84:5082–5086
48. Morris et al., 1988 Inhibin production by primary Sertoli cell-enriched cultures: regulation by follicle-stimulating hormone, androgens, and epidermal growth factor. Endocrinology 122:717–725
49. Krummen et al., 1994 Localization of inhibin and activin binding sites in the testis during development by in situ ligand binding. Biol Reprod 50:734–44
50. Hakovirta et al., 1993 Effects of Activin-A, Inhibin-A, and transforming growth factor-beta-1 on Stage-Specific deoxyribonucleic acid synthesis during rat seminiferous epithelial cycle. Endocrinology 133:1664–1668
51. van Dissel-Emiliani et al., 1989 Inhibin reduces spermatogonial numbers in testes of adult mice and Chinese hamsters. Endocrinology 125:1899–1903
52. Roberts V J, Barth S L, Meunier H, Vale W 1996 Hybridization histochemical and immunohistochemical localization of inhibin/activin subunits and messenger ribonucleic acids in the rat brain. J Comp Neurology 364:473–493
53. Schubert D et al., 1990 Activin is a nerve cell survival molecule. Nature, 344:868–870
54. Darland D C et al., 1995 Follistatin expression in developing targets of ciliary ganglion neurons suggests a role in regulating neurotransmitter phenotype. Neuron, 15:857–866
55. Schlessinger J et al., 1995 Regulation of Growth Factor Activation by Proteoglycans: What is the Role of the Low Affinity Receptors? Cell 83:357–360
56. Lopez-Casillas et al., 1993 Betaglycan presents ligand to the TGF beta signaling receptor. Cell 73:1435–44
57. Gunn T M et al., 1999 The mouse mahogany locus encodes a transmembrane form of human attractin. Nature 398:152–156
58. Nagle D et al., 1999 Nature, 398:148–152

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of augmenting activin-induced signaling in a cell comprising the step of:
    inhibiting the formation of inhibin/betaglycan complexes on the surface of said cell by an anti-betaglycan antiserum directed against an extracellular epitope of betaglycan.
2. The method of claim 1, wherein said cell is a pituitary cell.
3. The method of claim 2 wherein augmentation of activin signaling increases the production of Follicle Stimulating Hormone (FSH) by said cell.
4. The method of claim 3, wherein said method enhances fertility.

* * * * *

UNITED STATES PATENT AND TRADEMARK OFFICE
CERTIFICATE OF CORRECTION

PATENT NO.      : 6,692,744 B2
DATED           : February 17, 2004
INVENTOR(S)     : Vale et al.

It is certified that error appears in the above-identified patent and that said Letters Patent is hereby corrected as shown below:

Column 4,
Line 15, "compound" should read -- compounds --.
Line 23, please insert -- be -- between "may" and "peptides".
Line 60, "$^{121}$I" should read -- $^{125}$I --.
Line 63, "was" should read -- were --.

Column 5,
Line 10, "was" should read -- were --.
Line 40, please insert -- ™ -- after "Superfect".

Column 6,
Line 23, please close the quotation after "Manual".

Column 8,
Line 22, please insert -- of -- between "use" and "the".

Column 10,
Line 46, "prostrate" should read -- prostate --.
Line 65, "condititon" should read -- condititons --.

Column 13,
Line 16, "an" should read -- a -- .

Column 18,
Line 66, "ovine" should read -- bovine --.

Signed and Sealed this

Twenty-seventh Day of July, 2004

JON W. DUDAS
*Acting Director of the United States Patent and Trademark Office*